US012778722B2

(12) United States Patent
Stalcup et al.

(10) Patent No.: US 12,778,722 B2
(45) Date of Patent: Nov. 3, 2026

(54) DENTAL IMPLANT WITH POROUS INGROWTH MATERIAL

(71) Applicant: SMed-TA/TD, LLC, Columbia City, IN (US)

(72) Inventors: Gregory C. Stalcup, Fort Wayne, IN (US); Steve Dietzel, Warsaw, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 1272 days.

(21) Appl. No.: 17/126,562

(22) Filed: Dec. 18, 2020

(65) Prior Publication Data

US 2021/0186665 A1 Jun. 24, 2021

Related U.S. Application Data

(60) Provisional application No. 62/950,396, filed on Dec. 19, 2019.

(51) Int. Cl.

| | |
|---|---|
| ***A61C 8/00*** | (2006.01) |
| ***A61C 8/02*** | (2006.01) |
| ***A61L 27/06*** | (2006.01) |
| ***A61L 27/18*** | (2006.01) |
| ***A61L 27/54*** | (2006.01) |
| ***A61L 27/56*** | (2006.01) |

(52) U.S. Cl.

CPC .......... *A61C 8/0037* (2013.01); *A61C 8/0006* (2013.01); *A61L 27/06* (2013.01); *A61L 27/18* (2013.01); *A61L 27/54* (2013.01); *A61L 27/56* (2013.01); *A61C 2008/0046* (2013.01); *A61L 2430/12* (2013.01)

(58) Field of Classification Search

CPC ............................ A61C 8/0006; A61C 8/0037

See application file for complete search history.

(56) References Cited

U.S. PATENT DOCUMENTS

| | | | | |
|---|---|---|---|---|
| 4,439,152 | A | 3/1984 | Small | |
| 6,309,220 | B1 | 10/2001 | Gittleman | |
| 2005/0261778 | A1* | 11/2005 | Zelener | A61F 2/30734 623/23.26 |
| 2010/0003638 | A1* | 1/2010 | Collins | A61K 6/831 433/174 |
| 2010/0042215 | A1* | 2/2010 | Stalcup | A61B 17/866 606/86 R |
| 2013/0022943 | A1* | 1/2013 | Collins | A61C 8/0016 433/174 |
| 2014/0023992 | A1* | 1/2014 | Willis | A61K 6/84 433/174 |
| 2016/0015483 | A1 | 1/2016 | Kumar et al. | |
| 2017/0049536 | A1* | 2/2017 | Lomicka | A61C 8/0006 |

(Continued)

OTHER PUBLICATIONS

Osteosync, Sites Medical, 2018, https://web.archive.org/web/20180401070535/https://www.sitesmedical.com/proprietary-technologies/biosync-ti/ (Year: 2018).*

(Continued)

*Primary Examiner* — Ralph A Lewis

(74) *Attorney, Agent, or Firm* — TAYLOR & EDELSTEIN, PC

(57) ABSTRACT

A dental implant includes: a base having exterior surfaces and a plug opening formed therein; a plug assembly inserted into the plug opening; and at least one region of porous ingrowth material associated with at least one of the exterior surfaces of the base.

16 Claims, 5 Drawing Sheets

(56) References Cited

U.S. PATENT DOCUMENTS

| | | | | |
|---|---|---|---|---|
| 2017/0165036 | A1* | 6/2017 | Ceausu ................ | A61C 8/0045 |
| 2021/0186665 | A1* | 6/2021 | Stalcup ................ | A61C 8/0018 |
| 2022/0387143 | A1* | 12/2022 | Wysocki .............. | A61C 8/0013 |

OTHER PUBLICATIONS

Extended European Search Report dated Mar. 19, 2021 for European Patent Application No. 20214069.5 (6 pages).

* cited by examiner

DENTAL IMPLANT WITH POROUS INGROWTH MATERIAL

CROSS REFERENCE TO RELATED APPLICATIONS

This is a non-provisional application based upon U.S. provisional patent application Ser. No. 62/950,396, entitled "DENTAL IMPLANT WITH POROUS INGROWTH MATERIAL", filed Dec. 19, 2019, which is incorporated herein by reference.

BACKGROUND OF THE INVENTION

1. Field of the Invention

The present disclosure relates to dental implants and, more particularly, to dental implants incorporating features to encourage stable fixation following implantation.

2. Description of the Related Art

Dental implants are known that can be used to treat defect regions in a mouth of a patient. Known dental implants include a base portion that is fixated in the mouth before a replacement tooth is mounted to the base portion. Before the replacement tooth can be mounted to the base portion, the base portion must be firmly and stably fixated in the mouth. In many cases, the base portion is fixated in the mouth using, for example, fixation screws that are driven into solid tissue, such as tissue of the jawbone. Not only is this fixation painful for the patient, but such fixation is not always sufficient to hold the dental implant in place, which requires a revision surgery and additional pain and recovery time for the patient.

What is needed in the art is a reliable way to treat a defect region in a patient's mouth.

SUMMARY OF THE INVENTION

Exemplary embodiments disclosed herein provide dental implants that have porous ingrowth material on one or more surfaces of the implant to encourage tissue ingrowth into the material and fixation of the dental implant.

In some exemplary embodiments provided according to the present disclosure, a dental implant includes: a base having exterior surfaces and a plug opening formed therein; a plug assembly inserted into the plug opening; and at least one region of porous ingrowth material associated with at least one of the exterior surfaces of the base.

In some exemplary embodiments provided according to the present disclosure, a method of treating a defect region in a mouth include placing an implantation bore in the defect region and implanting a dental implant into the implantation bore. The dental implant includes: a base having exterior surfaces and a plug opening formed therein; a plug assembly inserted into the plug opening; and at least one region of porous ingrowth material associated with at least one of the exterior surfaces of the base and in contact with tissue of the defect region.

One possible advantage that may be realized by exemplary embodiments provided according to the present disclosure is that the region of ingrowth material can allow the implant to quickly fixate and stabilize in tissue of the defect region.

Another possible advantage that may be realized by exemplary embodiments provided according to the present disclosure is that the implant can be easily adjusted to treat both contained and uncontained defect regions.

Yet another possible advantage that may be realized by exemplary embodiments provided according to the present disclosure is that the base can include a reservoir to elute one or more therapeutic agents into the defect region and further increase the recovery speed.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DESCRIPTION OF THE INVENTION

Figure 1:
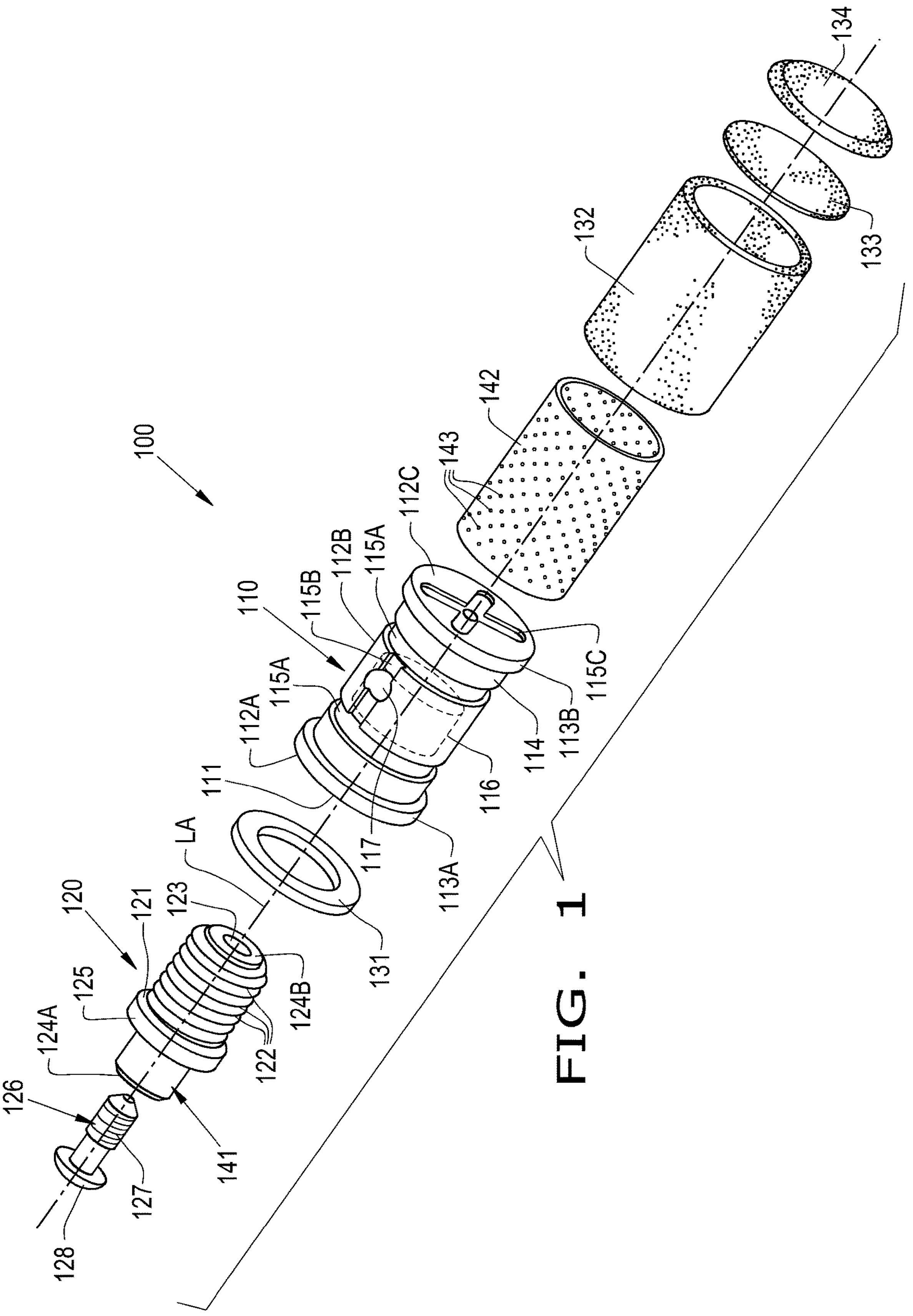
FIG. 1 is an exploded perspective view of an exemplary embodiment of a dental implant provided according to the present disclosure.
Figure 2:
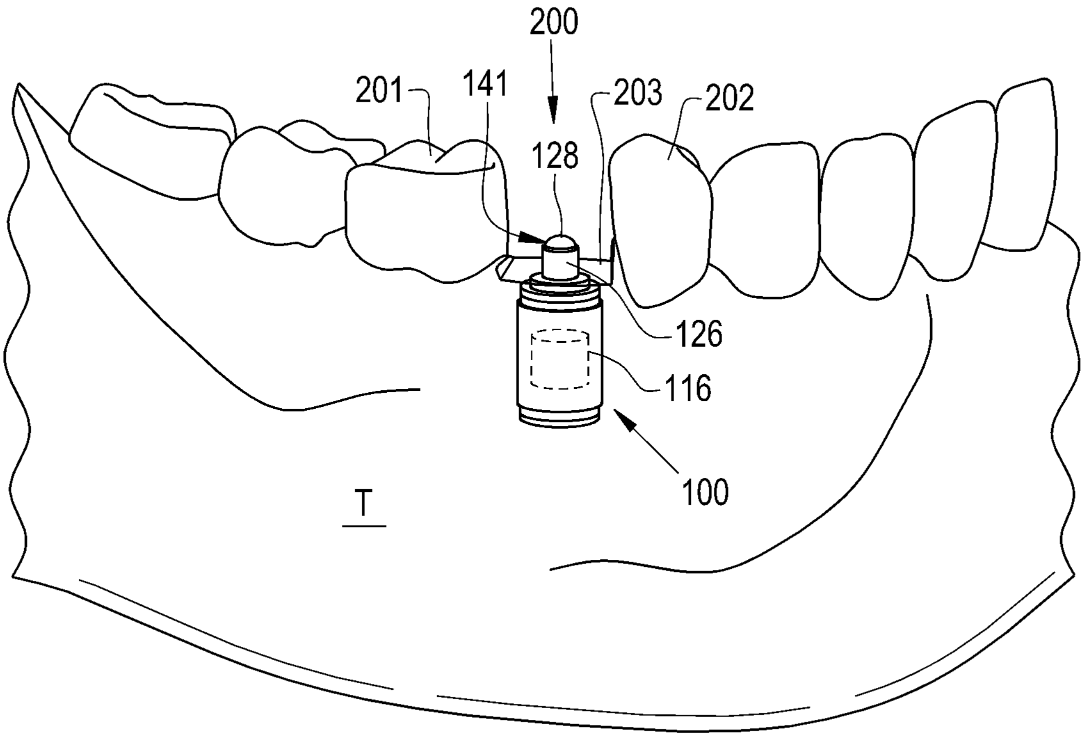
FIG. 2 is an illustration of the dental implant of FIG. 1 implanted in a defect region of a mouth of a patient.

Referring now to the drawings, and more particularly to FIGS. 1-2, an exemplary embodiment of a dental implant 100 for implantation within gingival tissue is illustrated. The dental implant 100 generally includes a base 110 with a plug opening 111 formed therein, a plug assembly 120 inserted into the plug opening 111, and at least one region of ingrowth material 131, 132, 133, 134, which are also referred to as "ingrowth regions," associated with one or more respective surfaces 112A, 112B, 112C of the base 110. In some embodiments, as illustrated in FIGS. 1-2, the base 110 defines a generally cylindrical shape with a pair of increased diameter ends 113A, 113B and a body portion 114 between and connecting the ends 113A, 113B. In some embodiments, the base 110 comprises a generally non-porous material, which may have a porosity of between about 0% and about 10%. The base 110 may comprise one or more biocompatible materials suitable for short-term or long-term placement within an animal body, human or otherwise, which can include, but are not limited to: metals such as titanium, stainless steel, cobalt chrome, and/or tantalum; polymers such as ultra-high molecular weight polyethylene (UHMWPE), other forms of polyethylene, polyether ether ketone (PEEK), polylactic acid (PLA), and/or polyglycolic acid (PGA); and/or ceramics such as hydroxyapatite (HA), high-density alumina, so-called "Bioglass," and graphite. It should be appreciated that all of the previously mentioned materials are exemplary only, and many other types of biomaterials can be incorporated in the base 110.

In some embodiments, one or more fluid delivery grooves 115A, 115B are formed in the body portion 114 to deliver fluid from a reservoir 116 formed inside the base 110 to surrounding tissue, as will be described further herein. The surfaces 112A and 112C of the base 110 may also include one or more respective fluid delivery grooves 115C. In some embodiments, two or more of the delivery grooves, such as grooves 115A, extend circumferentially about a longitudinal axis LA defined through the base 110 and one or more of the delivery grooves, such as groove 115B, extend parallel to the longitudinal axis LA to connect the circumferentially extending delivery grooves 115A. The shape and size of the delivery grooves 115A, 115B may be adjusted to give differing fluid delivery behavior from the reservoir 116 of the implant 100 to surrounding tissue. The fluid delivery grooves 115A, 115B may fluidly communicate with the reservoir 116 formed in the base 110 via a reservoir opening 117 that is formed in the base 110 to the reservoir 116 and partially surrounded by the delivery groove 115B.

A plug assembly 120 is inserted into the plug opening 111 of the base 110 to close the plug opening 111. In some embodiments, the plug assembly 120 comprises a base engaging portion 121 with threads 122 that thread into corresponding threads of the base 110 to couple the base engaging portion 121 with the base 110. The base engaging portion 121 may have a through-hole 123 extending therethrough that extends from one end 124A of the base engaging portion 121 to an opposite end 124B. In some embodiments, a stop 125 is formed in the base engaging portion 121 between the ends 124A, 124B to prevent the base engaging portion 121 from over-threading into the base 110. The base engaging portion 121 may be unthreaded on one side of the stop 125, such as adjacent to the end 124A, and threaded on the other side of the stop 125, such as adjacent to the end 124B.

The plug assembly 120 may further include a plug portion 126 that is placed in the through-hole 123 of the base engaging portion 121. The plug portion 126 may, for example, include a stem 127 with a diameter less than a diameter of the through-hole 123 and a head 128 having a diameter greater than the diameter of the through-hole 123 that is connected to the stem 127. In some embodiments, the plug portion 126 may comprise a generally inelastic material, such as a thermoset polymer. Alternatively, the plug portion 126 may comprise an elastic material, such as rubber. It should be appreciated that the plug portion 126 should sufficiently fill the through-hole 123 of the base engaging portion 121 to plug the through-hole 123 so fluid from the reservoir 116 does not rapidly leak out of the through-hole 123 when subjected to increase fluid pressure.

In some embodiments, the through-hole 123 is formed in a mount 141 of the base engaging portion 121 that is shaped and sized to mount, for example, a replacement tooth thereon. In other words, the plug assembly 120 is configured to mount a replacement tooth thereon. The replacement tooth may fit directly on the mount 141 for fixation within the patient or, alternatively, an adapter may be fit on the mount 141, with the replacement tooth then being mounted to the adapter. Many such mounts for replacement teeth are known, so further description of the mount 141 is omitted for brevity.

At least one region of ingrowth material, illustrated as four regions 131, 132, 133, 134, is associated with one or more respective surfaces 112A, 112B, 112C of the base 110. As used herein, the ingrowth regions 131, 132, 133, 134 are "associated with" a respective surface of the base 110 in the sense that each ingrowth region 131, 132, 133, 134 is directly or indirectly fixated to its respective surface 112A, 112B, 112C of the base 110. To encourage tissue ingrowth, the ingrowth material of each region 131, 132, 133, 134 is porous and comprises a biocompatible material. Each region 131, 132, 133, 134 may comprise the same ingrowth material or, alternatively, one or more of the regions 131, 132, 133, 134 may comprise a different ingrowth material than one or more of the other regions 131, 132, 133, 134. In some embodiments, the ingrowth material comprises titanium or polyether ether ketone (PEEK) having a porosity of between about 50% and 70%, a mean pore size of between about 500 μm and about 550 μm, a pore interconnectivity of between about 210 μm and about 250 μm, and a nominal thickness of between about 0.25 mm and 1.25 mm. One exemplary ingrowth material that may be used in one or more of the regions 131, 132, 133, 134 is commercially available under the tradename OSTEOSYNC® from SITES MEDICAL® of Columbia City, Indiana. It should be appreciated that these characteristics of the ingrowth material(s) are exemplary only. In some embodiments, one of the regions, such as region 131, is associated with the top surface 112A of the base 110; one of the regions, such as region 132, is associated with the circumferential surface 112B of the base 110 between terminal end regions 113A, 113B of the base 110, which are not covered by any ingrowth material; and two of the regions, such as regions 133 and 134, are associated with the bottom surface 112C of the base 110. Each of the surfaces 112A, 112B, 112C may have a through-hole formed through to the reservoir 116 to allow fluid delivery from the reservoir 116 to surrounding tissues through pores of the ingrowth regions 131, 132, 133, 134.

In some embodiments, two of the ingrowth regions associated with the same surface, such as the ingrowth regions 133 and 134 associated with the bottom surface 112C of the base 110, differ from one another. For example, the ingrowth region 133, which may be referred to as a "first region of ingrowth material" and sandwiched between the ingrowth region 134 and the bottom surface 112C of the base 110, may comprise a first ingrowth material that has a lower porosity compared to a second ingrowth material of the ingrowth region 134, which may be referred to as a "second region of ingrowth material." In other words, the first ingrowth material of the first region of ingrowth material 133 may have a first porosity and the second ingrowth material of the second region of ingrowth material 134 may have a second porosity that differs from the first porosity, e.g., by being greater than the first porosity. By providing the ingrowth region 133 with a lower porosity than the ingrowth region 134, the fluid delivery rate to surrounding tissues from the reservoir 116 may be limited by the porosity of the ingrowth region 133 while the porosity of the ingrowth region 134 may be greater to encourage tissue ingrowth into the pores of the ingrowth region 134. Such a configuration can allow long-term fluid delivery from the reservoir 116 to surrounding tissue, due to the relatively low porosity of the ingrowth region 133, while providing larger pores in the ingrowth region 134 to encourage tissue ingrowth to stabilize the implant 100. Alternatively, or in addition to, the two ingrowth regions 133, 134 may differ from one another by, for example, having different compositions and/or shapes. It should be appreciated that ingrowth regions associated with the same surface may differ from each other in other ways, and the foregoing examples represent only a few of the possible ways that the regions may differ from each other.

In some embodiments, a perforated sleeve 142 is placed between the circumferential surface 112B of the base 110 and the ingrowth region 132 to provide a uniform surface for associating the ingrowth region 132 with the circumferential surface 112B. As illustrated in FIG. 1, the circumferential surface 112B may be relatively non-uniform due to the formation of the fluid delivery grooves 115A, 115B, which makes securing the ingrowth region 132 to the surface 112B difficult. The perforated sleeve 142, therefore, fits on the circumferential surface 112B, such as by press fitting, between the terminal end regions 113A, 113B of the base 110 to provide a uniformly sized surface for securing the ingrowth region 132. Further, the size of apertures 143 formed in the perforated sleeve 142 may be adjusted to control fluid delivery through pores of the ingrowth region 132 by controlling the rate of fluid flow to the ingrowth region 132 from the reservoir 116 via the reservoir opening 117. In this respect, the perforated sleeve 142 assists with associating the ingrowth region 132 with the circumferential surface 112B of the base 110 as well as controlling fluid delivery from the reservoir 116 to surrounding tissues following implantation.

Referring specifically now to FIG. 2, the implant 100 is illustrated following implantation into gingival tissue T of a mouth of a patient, which may be a human or other animal. As illustrated in FIG. 2, a defect region 200 is present between two adjacent teeth 201, 202 in the patient. The defect region 200 previously held a tooth, which has fallen out or otherwise been removed due to, for example, disease or trauma. To replace the tooth, the defect region 200 is cleaned to remove remaining fragments of the removed tooth, other debris, and pathogens. In the case illustrated in FIG. 2, the defect region 200 is a contained defect that has sufficient amounts of local gingival and bone tissue to support and fixate the implant 100 without requiring, for example, one or more screws anchoring the implant 100.

An implantation bore 203 is formed in the tissue of the defect region 200 and the implant 100 is placed within the implantation bore 203. In some embodiments, the implantation bore 203 is formed by removing the tooth (or tooth fragments) that is present in the defect region 200 and is being replaced by the implant 100. As illustrated, the mount 141 protrudes out of the implantation bore 203 following placement of the implant 100 to accept, for example, a replacement tooth after the implant 100 has sufficiently fixated within the tissue. Initially, however, the mount 141 may be left uncovered in the defect region 200, exposing the mount 141 and the head 128 of the plug portion 126. Before, during, or after implantation, the plug portion 126 may be removed from the through-hole 123 in the mount 141 and one or more therapeutic agents may be filled into the reservoir 116 within the base 110 via the through-hole 123. The therapeutic agent(s) may be, but is not limited to, an antibiotic or other antimicrobial agent, an anti-inflammatory agent, an analgesic, a growth factor, a solution comprising regenerative cells such as stem cells, or any other substance that provides a therapeutic effect on the tissue surrounding the implant 100 following implantation. Alternatively, the therapeutic agent(s) may be filled into the reservoir 116 via, for example, the reservoir opening 117 prior to covering the reservoir opening 117 with the perforated sleeve 142 and the ingrowth region 132. Thus, it should be appreciated that the reservoir 116 may be initially filled with one or more therapeutic agents in a variety of ways.

In some embodiments, the reservoir 116 is initially filled with a first therapeutic agent, which may be one or more antimicrobial agents to reduce the risk of infection, and then refilled with the first therapeutic agent, a second therapeutic agent that is different from the first therapeutic agent, or both while the implant 100 is implanted in the patient. For example, the reservoir 116 may be refilled partially with the first therapeutic agent (an antimicrobial) to continue delivering antimicrobial agent to surrounding tissue to reduce the risk of infection but also filled with a second therapeutic agent, such as a growth factor, to encourage tissue infiltration and ingrowth into the ingrowth regions 131, 132, 133, 134 to encourage a faster and more stable fixation of the implant 100 in the defect region 200. To refill the reservoir 116, the plug portion 126 may be pulled out of the through-hole 123 and a tip of a syringe containing the therapeutic agent(s) placed within the through-hole 123 to inject the therapeutic agent(s) from the syringe into the through-hole 123 and the fluidly coupled reservoir 116. Alternatively, the syringe may also be used to remove fluid, which may be therapeutic agent or biological fluid, from the reservoir 116.

After partially or fully filling the reservoir 116, the plug portion 126 is replaced in the through-hole 123. In some embodiments, the plug portion 126 is shaped and sized such that replacement of the plug portion 126 in the through-hole 123 pressurizes the fluid in the reservoir 116, urging the fluid in the reservoir 116 out to the ingrowth regions 131, 132, 133, 134 via, for example, the reservoir opening 117 formed in the base 110. In this respect, the plug portion 126 not only seals the through-hole 123, but also provides an initial pressurization of the reservoir 116 to deliver a bolus of the therapeutic agent(s) to surrounding tissue while the implant 100 is implanted in the patient. After the initial bolus of therapeutic agent(s) is delivered, the remaining therapeutic agent(s) in the reservoir 116 may then travel out of the reservoir 116 into the surrounding tissue by compressive force exerted on the implant 100 "squeezing" out the therapeutic agent(s) as well as by natural diffusion of the therapeutic agent(s) into the tissue. It should be appreciated that the plug portion 126 may be removed from and replaced in the through-hole 123 multiple times throughout the implantation to refill the reservoir 116. Due to the simplicity of removing and replacing the plug portion 126 to refill the reservoir 116, the patient in which the implant 100 is implanted may refill the reservoir 116 at home or in other non-clinical settings.

While the implant 100 is implanted, native tissues adjacent to the defect region 200, such as gingival tissue and bone tissue, may infiltrate and grow into the ingrowth regions 131, 132, 133, 134 of the implant 100. As the native tissues grow into the ingrowth regions 131, 132, 133, 134, the implant 100 becomes stably fixated within the tissue. After the implant 100 is stably fixated within the tissue, the replacement tooth may be mounted to the mount 141 to finish replacement of the removed tooth. In some embodiments, the replacement tooth may be mounted directly on the mount 141 with the plug portion 126 placed in the through-hole 123 of the base engaging portion 121. In some embodiments, the plug portion 126 may be replaced with a different plug in the through-hole 123 that is shaped to both fill the through-hole 123 and engage, for example, a socket of the replacement tooth to mount the replacement tooth to the mount 141. In other embodiments, the base engaging portion 121 may be replaced with a different base engaging portion having a mount for mounting the replacement tooth. It should thus be appreciated that many different ways of mounting a replacement tooth to the implant 100 may be used to fixate the replacement tooth to the implant 100.

It has been discovered that certain ingrowth materials, such as the previously described OSTEOSYNC®, provide surprisingly good tissue ingrowth and fixation characteristics to the implant 100. When OSTEOSYNC® is used to form the ingrowth regions 131, 132, 133, 134, the push-out strength of the implant 100 may be roughly equivalent to the push-out strength of native bone after only 5 weeks of implantation. The results were surprising because of the high degree of improvement that such an implant provided compared to known dental implants. Without being bound to any particular theory as to why such results were observed, it is theorized that the ingrowth regions 131, 132, 133, 134, when comprising OSTEOSYNC® or similar materials, provide an excellent substrate for cortical bone tissue ingrowth. Considering the high concentration of cortical bone tissue adjacent to the jawbone, it is theorized that the stable fixation of the implant 100 at five weeks is at least partly attributable to rapid ingrowth and proliferation of cortical bone tissue in the ingrowth regions 131, 132, 133, 134. It is thus theorized that implants provided in accordance with the present disclosure are well-suited as dental implants because they simulate the natural fixation of teeth in the gingival tissue and the bone tissue present in the mouth of a patient, i.e., predominantly by ingrowth of and integration with adjacent cortical bone tissue.

It has also been found that providing one or more therapeutic agents in the reservoir 116 for therapeutic agent delivery during implantation encourages rapid, stable fixation of the implant 100. As previously described, the reservoir 116 may be initially filled with one or more antimicrobial agents to reduce the risk of pathogens infecting the defect region 200 and interfering with tissue growth fixating the implant 100. The reservoir 116 may be refilled one or more times with the antimicrobial agent(s), or other therapeutic agent(s), throughout the implantation, as previously described, to encourage tissue ingrowth into the ingrowth regions 131, 132, 133, 134 and stable fixation of the implant 100. Therefore, the implants provided in accordance with the present disclosure may also encourage rapid, stable fixation in the surrounding native tissue by delivering one or more therapeutic agents into the surrounding tissue from the reservoir 116 to provide a favorable environment for tissue ingrowth into the ingrowth regions 131, 132, 133, 134.

Figure 3:
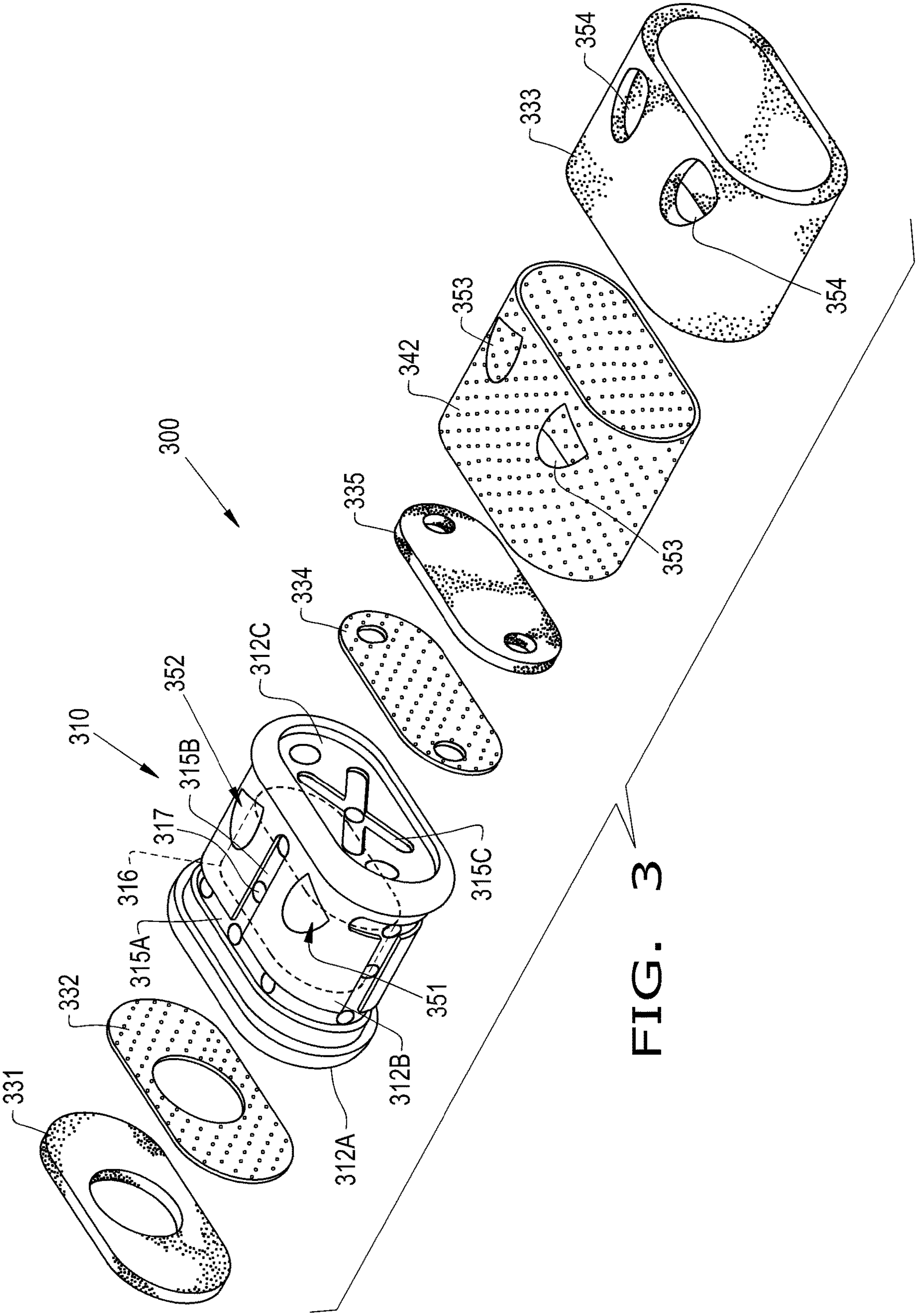
FIG. 3 is an exploded perspective view of another exemplary embodiment of a dental implant provided according to the present disclosure.
Figure 4:
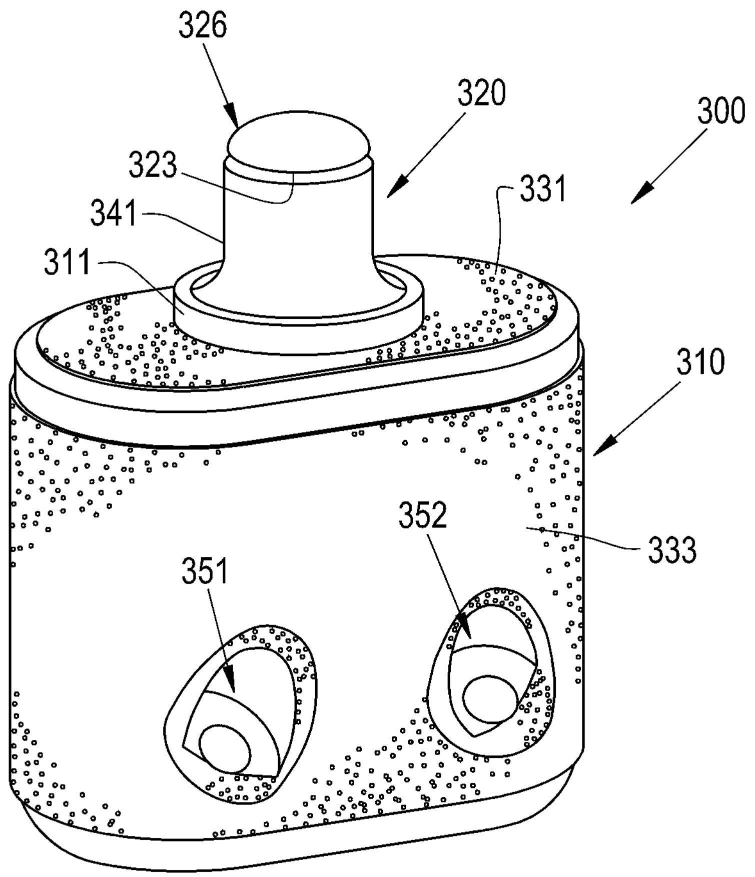
FIG. 4 is a perspective view of the dental implant of FIG. 3.
Figure 5:
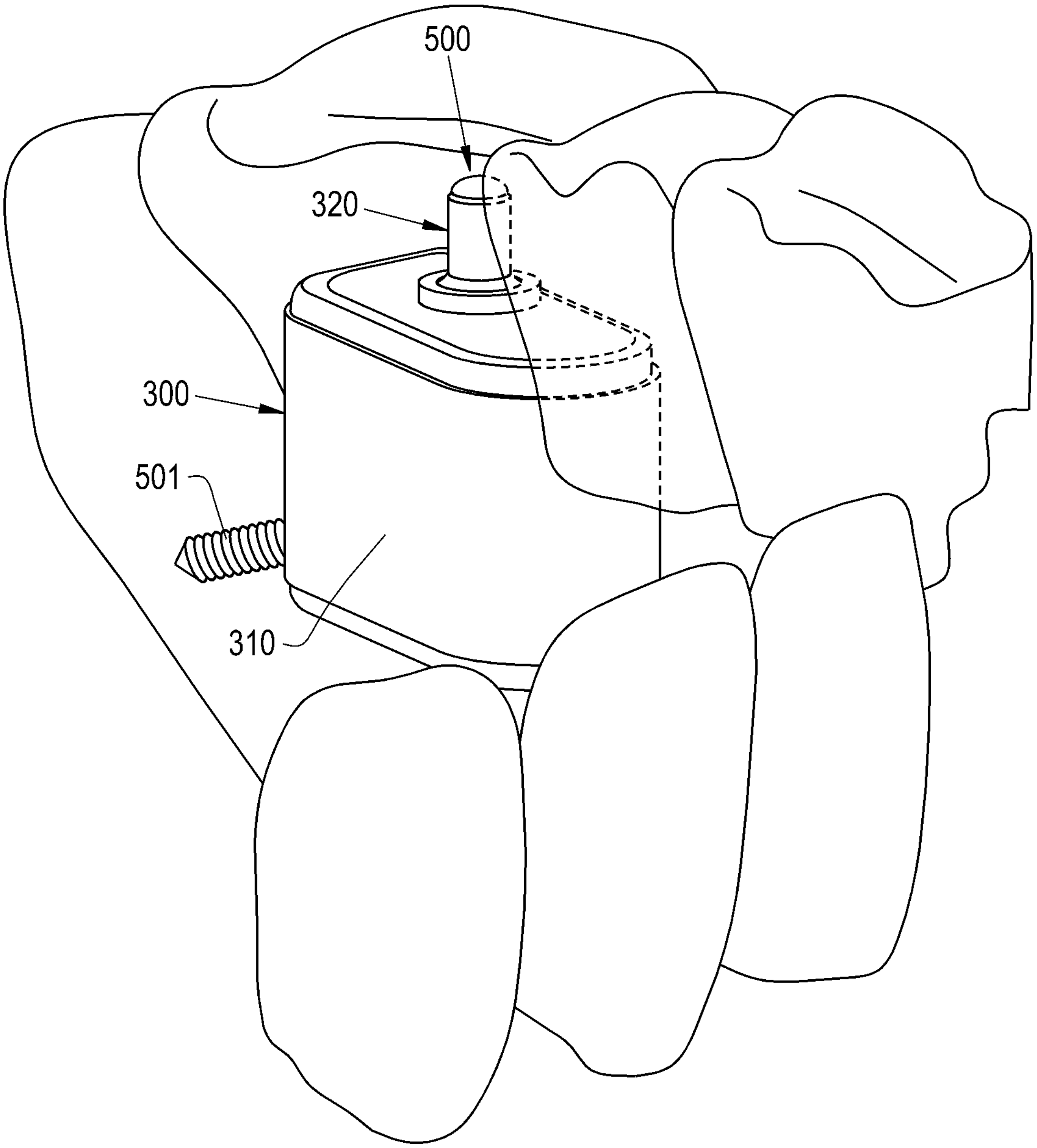
FIG. 5 is an illustration of the dental implant of FIGS. 3-4 implanted in a defect region of a mouth of a patient.

Referring now to FIGS. 3-5, another exemplary embodiment of a dental implant 300 for implantation within gingival tissue that has an uncontained defect is illustrated. Similarly to the previously described implant 100, the implant 300 includes a base 310 with a plug opening 311 formed therein, a plug assembly 320 inserted into the plug opening 311, and at least one region of ingrowth material 331, 332, 333, 334, 335 associated with one or more respective surfaces 312A, 312B, 312C of the base 310. As illustrated in FIG. 3, for example, the ingrowth regions 331 and 332 may be associated with the top surface 312A of the base 310; the ingrowth region 333 may be associated with the peripheral surface 312B of the base 310; and the ingrowth regions 334 and 335 may be associated with the bottom surface 312C of the base 310. Compared to the implant 100, with a cylindrical base 110 having a generally circular cross-section, the implant 300 has a relatively larger base 310 with an oval cross-section to stabilize the implant 300 in an uncontained defect region 510, which is illustrated in FIG. 5 and described further herein.

Similarly to the base 110, the base 310 can have fluid delivery grooves 315A, 315B, 315C formed therein that communicate fluid from a reservoir 316 formed in the base 310 to, for example, the ingrowth regions 331, 332, 333, 334, 335 via openings, such as a reservoir opening 317, formed in the base 310 to the reservoir 316. The reservoir 316 may be refilled by removing a plug portion 326 from the plug assembly 320 and delivering fluid to the reservoir 316 through a through-hole 323 of the plug assembly 320 using, for example, a syringe or other fluid delivery device. The implant 300 may also include a perforated sleeve 342 between the ingrowth region 333 and the circumferential surface 312B and have a mount 341 for mounting a replacement tooth, similarly to the implant 100.

The implant 300 is configured to be implanted in an uncontained defect, i.e., a defect where adjacent tissue is diseased, destroyed, and/or otherwise unsuitable for fixating the implant 300 without additional fixation. To provide the additional fixation needed to stably fixate the implant 300, one or more fixation openings 351, 352 may be formed in the base 310, such as in the circumferential surface 312B, to accept a respective fixator, such as one or more orthopaedic screws 501 (illustrated in FIG. 5). Corresponding openings 353, 354 may also be formed in the perforated sleeve 342 and the ingrowth region 333 so the fixation openings 351, 352 are uncovered to accept the screw(s) 501. The fixation opening(s) 351, 352 may be, for example, threaded to couple with the screw(s) 501 in order to fixate the implant 300 within the mouth of the patient. In this respect, implantation and use of the implant 300 is similar to that of the implant 100, but also includes the additional step of fixating the fixator(s) 501 in a defect region, such as defect region 500 illustrated in FIG. 5, and coupling the fixator(s) 501 with the implant 300 by, for example, threading the fixator(s) 501 into the fixation opening(s) 351, 352. In all other respects, implantation and use of the implant 300 may be similar to implantation and use of the implantation 100, which is previously described.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dental implant, comprising:
- a base having exterior surfaces and a plug opening formed therein;
- a plug assembly inserted into the plug opening;
- at least one region of porous ingrowth material associated with at least one of the exterior surfaces of the base; and
- a perforated sleeve disposed between the base and the at least one region of porous ingrowth material, the perforated sleeve being fit on the at least one of the exterior surfaces of the base between two terminal end regions of the base to provide a uniform surface for associating the at least one region of porous ingrowth material with the at least one of the exterior surfaces of the base.

2. The dental implant of claim 1, wherein the plug assembly is configured to have a replacement tooth mounted thereon.

3. The dental implant of claim 1, wherein the perforated sleeve is press fit to the base.

4. The dental implant of claim 1, wherein the base has a reservoir formed therein that is configured to hold a fluid therein.

5. The dental implant of claim 4, wherein the base has at least one fluid delivery groove formed therein that is in fluid communication with the reservoir.

6. The dental implant of claim 4, wherein the at least one of the exterior surfaces of the base associated with the at least one region of ingrowth material has a through-hole formed therein that extends into the reservoir.

7. The dental implant of claim 1, wherein the base comprises a generally non-porous material.

8. The dental implant of claim 1, wherein the at least one region of ingrowth material comprises an ingrowth material having a porosity of between 50% and 70%.

9. The dental implant of claim 8, wherein the ingrowth material comprises titanium or polyether ether ketone.

10. The dental implant of claim 1, wherein a first region of ingrowth material and a second region of ingrowth material are associated with a same exterior surface, the first region of ingrowth material comprising a first ingrowth material and the second region of ingrowth material comprising a second ingrowth material that differs from the first ingrowth material.

11. The dental implant of claim 10, wherein the first ingrowth material has a first porosity and the second ingrowth material has a second porosity that differs from the first porosity.

12. The dental implant of claim 11, wherein the first region of ingrowth material is sandwiched between the base and the second region of ingrowth material and the first porosity is less than the second porosity.

13. The dental implant of claim 1, wherein the base has a circular cross-section.

14. The dental implant of claim 1, wherein the base has an oval cross-section.

15. The dental implant of claim 1, wherein the base comprises at least one fixation opening configured to accept a fixator to fixate the dental implant within gingival tissue.

16. The dental implant of claim 15, wherein the at least one fixation opening is uncovered.

* * * * *